United States Patent [19]
Filho

[11] Patent Number: 6,089,867
[45] Date of Patent: Jul. 18, 2000

[54] TOOTH IMPLANT AND METHOD FOR IMPLANTATION

[76] Inventor: Ney de Souza Blazzio Filho, SCS Ed. Carioca SL 407, Brasilia D.F., Brazil

[21] Appl. No.: 09/039,415

[22] Filed: Mar. 16, 1998

[51] Int. Cl.[7] ................................................ A61C 8/00
[52] U.S. Cl. .................................... 433/215; 433/175
[58] Field of Search .................................. 433/215, 218, 433/219, 229, 172, 173, 174, 175, 176, 201.1; 623/16

[56] References Cited

U.S. PATENT DOCUMENTS

| | | | |
|---|---|---|---|
| 3,934,347 | 1/1976 | Lash et al. | 32/10 A |
| 4,277,238 | 7/1981 | Katagiri | 433/201.1 |
| 4,689,014 | 8/1987 | Krasner | 433/175 X |
| 5,004,422 | 4/1991 | Propper | 433/175 |
| 5,112,354 | 5/1992 | Sires | 623/16 |

*Primary Examiner*—Nicholas D. Lucchesi
*Attorney, Agent, or Firm*—Bacon & Thomas

[57] ABSTRACT

This invention pertains to a tooth implant which is obtained from a donor's jawbone. The tooth implant includes the root of the donor's tooth with the crown detached therefrom and a portion of the donor's jawbone which surrounds the root and is attached thereto. The implant is obtained by carefully harvesting the root with the attached portion of jawbone surrounding the root as a single unit from a donor individual. The tooth implant is implanted into an opening in a recipient's jawbone. Upon healing, the implant is firmly and permanently attached to the bone tissue of the recipient. The root of the implant may then be used to affix a prosthetic crown within the jawbone of the recipient.

13 Claims, 2 Drawing Sheets

TOOTH IMPLANT AND METHOD FOR IMPLANTATION

BACKGROUND OF THE INVENTION

1. Field of the Invention

This invention relates to the field of dentistry and oral surgery. More particularly, this invention pertains to the art of tooth implants and the use thereof in the jawbone of an individual in order to replace teeth which have been lost by extraction or injury or which are otherwise missing from the jawbone.

2. Background Information

Proper dentition is highly desirable for adequate mastication of food and operation of the jaw. Thus, proper dentition is important from a nutritional point of view. It is also important for cosmetic purposes. When one or more teeth are missing from a person's jawbone, for example, due to a previous extraction or injury, it is important for the patient's well being to replace the missing tooth or teeth to restore proper dentition.

Various methodologies have been used in the past to replace missing teeth. In general, these procedures require anchoring the replacement tooth into the jawbone (maxilla or mandible). For this purpose, various types of anchoring devices have been developed for retaining the replacement tooth so that it is immobilized in the jawbone. However, these devices often fail to adequately hold the tooth in place and consequently such failure would typically lead to infection and/or rejection of the implanted tooth.

Attempts have been made to use bone graft techniques to assist in the formation of a strong foundation for later inserting a prosthetic tooth without causing rejection symptoms. In particular, U.S. Pat. No. 4,277,238 discloses a bone graft which can act as a spacer for a missing tooth or can serve as a foundation for a false tooth. However, the technique described in the aforementioned patent requires insertion of porous bone graft material into the existing socket of the missing tooth so that the porous bone graft material eventually becomes ossified whereby the ossified implant conforms to the shape of the socket previously occupied by the root of the missing tooth. Thus, instead of using a natural root, this technique replaces the root of the missing tooth with bone graft material which is inferior to the genuine root of a natural tooth. Furthermore, this prior art technique limits the space for the implant by confining it to the geometric space defined by the socket with the periodontal membrane left in place.

In view of the above inadequacies of the prior art, a need remains in the art to provide a tooth implant and method of implantation wherein the implant includes the natural root of a tooth which can serve to anchor an upper replacement part (i.e. crown) of a tooth.

SUMMARY OF THE INVENTION

It is an object of this invention to provide an improved tooth implant containing the root of a natural tooth and surrounding bone tissue which is useful for replacing a missing tooth by implantation into a site in the jawbone specifically adapted to receive the implant.

It is a further object of this invention to provide a method for implanting a tooth implant containing the root of a natural tooth and surrounding bone tissue.

It is a further object of this invention to provide a method for making a tooth implant which contains the root of a natural tooth.

These and other objectives are achieved by a particular process which involves harvesting the implant from a donor, preparing the implant for implantation into the jawbone, surgically preparing the site in the jawbone for implantation and implanting the harvested implant into the prepared site.

The implant obtained from the donor comprises the root and surrounding bone of a tooth. The implant containing the root and surrounding bone is harvested as a single unit wherein the root is circumscribed by bone from the donor. The amount and shape of the surrounding bone is selected so as to fit into a correspondingly shaped opening in the jawbone of the recipient. The term "jawbone" as used herein includes the upper jaw or maxilla and the lower jaw or mandible.

The opening in the jawbone of the recipient is prepared by carefully cutting away the bone to produce an opening therein which is large enough to receive the implant. Preferably the opening is prepared having a shape which corresponds to the shape of the implant but is sized slightly larger than the implant so that the implant can fit into the opening. The opening should be slightly larger than the implant to provide space which can be filled with the recipient's blood when the implant is in place in the opening so that the blood within this space will clot therein. The blood clot is crucial to the integration of the implant by the living bone of the recipient. Preferably the implant is removed from the donor by making a cut around the tooth and extending the cut along the axis of the tooth into the jawbone so that it may be removed as a bone plug containing the root. The opening in the jawbone of the recipient may be formed in the same manner. Conventional surgical saws, such as cylindrical surgical saws, may be used for this purpose.

In most instances, the donor will be a deceased person (e.g., cadaver) in which case the donor and recipient will be different individuals. However, this invention may also be practiced when the donor and recipient are the same individual such as when a tooth from one location in the jawbone serves as a source for an implant which is to be implanted in another location in the jawbone of the same individual.

After implantation, the bone of the implant is integrated by the living bone of the recipient by calcification or osseointegration as bone forming cells invade the clot within the space around the implant. The integration of the bone occurs during the healing process which begins after the surgery. Integration of the bone results in the implant being permanently affixed to the surrounding recipient bone by means of rigid bonding calcification between the recipient's bone and the implanted bone.

Normally, the natural crown is removed from the tooth which is used for the implant since it is only the root and surrounding bone which is necessary to practice this invention. Thus, the implant which has the root or roots of a natural tooth can then serve as a foundation for an artificial or prosthetic crown which can be attached to the implant after the implantation has been completed. Any root canal work which is required as a prerequisite for attachment of a crown or for other surgical procedures should be done prior to implantation. In the case where the donor is the recipient, the required root canal work should be done before harvesting since in this situation, implantation of the implant is performed immediately after harvesting.

BRIEF DESCRIPTION OF THE DRAWINGS

FIG. 2 also shows the use of a cylindrical saw which is used to remove the implant from the jawbone.

DETAILED DESCRIPTION OF THE INVENTION AND PREFERRED EMBODIMENT

Figure 1:
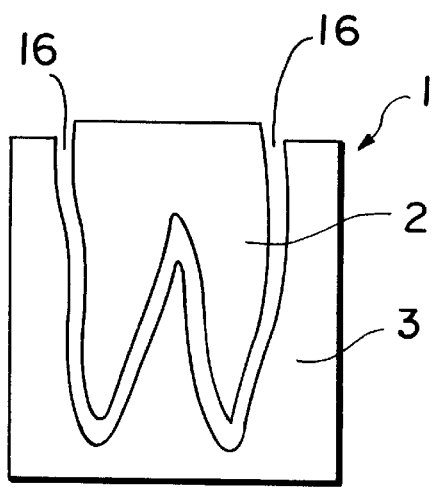
FIG. 1 is a cross-sectional representation of a tooth implant of this invention.
Figure 1B:
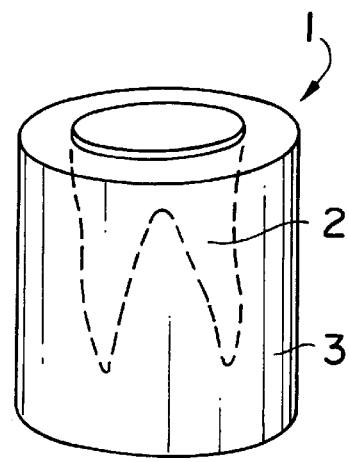
FIG. 1B is a perspective view of a tooth implant made in accordance with this invention.
Figure 2:
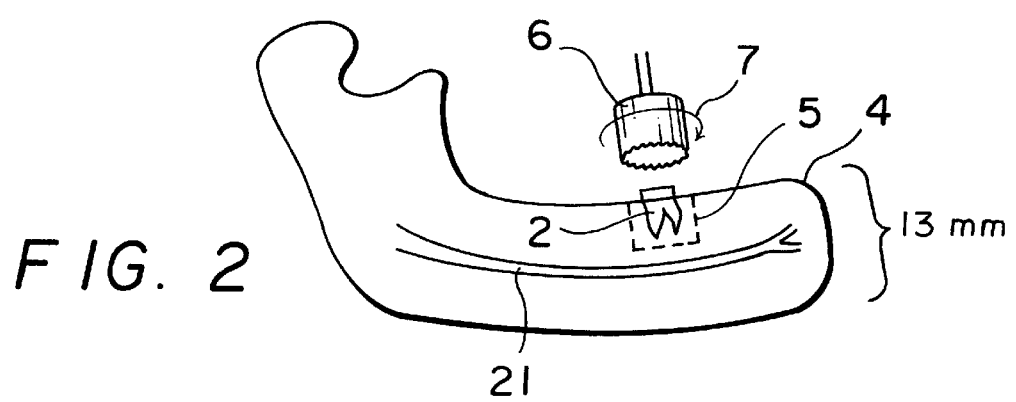
FIG. 2 is the lower jawbone (mandible) of a donor from which the implant of this invention is derived.

In a preferred embodiment, the implant is obtained from a deceased donor by carefully cutting out the root circumscribed with attached bone. For example, the implant shown generally by reference numeral 1 in FIG. 1 is removed from the donor's jawbone 4 (shown in FIG. 2) by making a cut around the root extending downward along dashed line 5 so as to form a root 2 circumscribed by a portion of donor bone 3. A cut may be made by saw 6 rotating in the direction of arrow 7 as shown in FIG. 2. The cut would be made in an upward direction if the tooth were being removed from the upper jawbone or maxilla. In either case, the cut is made into the jawbone around the tooth in the direction of the axis of the tooth so that the entire root with a portion of the donor jawbone attached thereto can be removed as a single unit. Removal of the root circumscribed by the donor bone as a unit results in an implant in the form of a plug as shown in the perspective view in FIG. 1A. Removal of the implant creates a hole or opening defined by dashed line 5 in FIG. 2.

The saw illustrated in FIG. 2 is cylindrical and thereby results in the formation of a cylindrical implant. However the cylindrical shape is not critical to the invention and the implant can be removed from the donor's bone by other methods which do not necessarily result in a cylindrical implant.

The crown may be removed prior to harvesting so that the harvested part contains the root 2 circumscribed by donor bone 3 as shown in FIG. 1 without any crown being attached thereto. After the implant is removed from the deceased donor, it is treated for storage so that it can be kept for later use. Implants may thus be collected and logged by size, type, etc. and stored in a tooth bank for later implantation in a recipient when the demand arises.

A root canal procedure must be performed on the implant tooth prior to implantation in order to remove undesirable tissue such as blood vessels, nerve tissue, lymphatic vessels, etc. The root canal procedure may be performed either before or after lyophilization. Preferably the implant is lyophilized after the root canal is cleansed of tissue but before the cleansed canal is filled. The preferable order of steps is as follows:

1. obtaining a donor
2. selecting or obtaining the implant
3. opening an instrumentation of the root canal
4. lyophilization of the implant
5. closing or filling of the root canal Preferably, if any root canal work is needed, it is done prior to treatment for storage. Conventional treatment, such as is used for bio-implantable bone blades and powdered bone, is useful for the implant of this invention. Thus, treatment of the implant includes washing and/or rinsing, removal of all connected tissue, lyophilization and sterilization. A separate sterilization step is not needed if the lyophilization procedure results in sterility. For example, the implant may be treated by the process disclosed in U.S. Pat. No. 5,112,354 and lyophilized and stored in a sterile condition in sterile containers. The implant may also be treated in accordance with the treatment described in U.S. Pat. No. 4,277,238. The disclosure of U.S. Pat. Nos. 5,112,354 and 4,277,238 are incorporated herein by reference.

Structure surrounding the root of the implant derived from a deceased person such as the periodontal membrane and fibers normally found in the space 16 between the root and the jawbone will normally be removed when the implant is treated for storage. For illustration purposes, space 16 has been exaggerated in FIG. 1.

When a patient is to receive an implant from a tooth bank, it is necessary to prepare the opening in the jawbone of the recipient before surgical implantation. The opening in the recipient's jawbone (maxilla or mandible) is made during the surgical procedure in which implantation takes place so that freshly clotted blood is present in the opening during implantation. The blood clot is beneficial because it aids in the growth of new bone tissue which is required for firm attachment of implant bone tissue to the recipient's bone.

Preferably the implant is immersed in blood prior to implantation so that blood can penetrate small pores or openings contained in the bone of the implant. The blood in which the implant is immersed is taken from the recipient. In order to aid in the penetration of the blood into the bone pores or cavities of the implant, the blood may be treated with an anticoagulant. In order to further enhance the penetration of the blood into the pores or cavities of the implant bone, the bone, while it is immersed in the blood may be subjected to a vacuum or partial vacuum. This may be accomplished by immersing the bone in a container of blood treated with an anticoagulant and then placing the container in a vacuum chamber.

Figure 3:
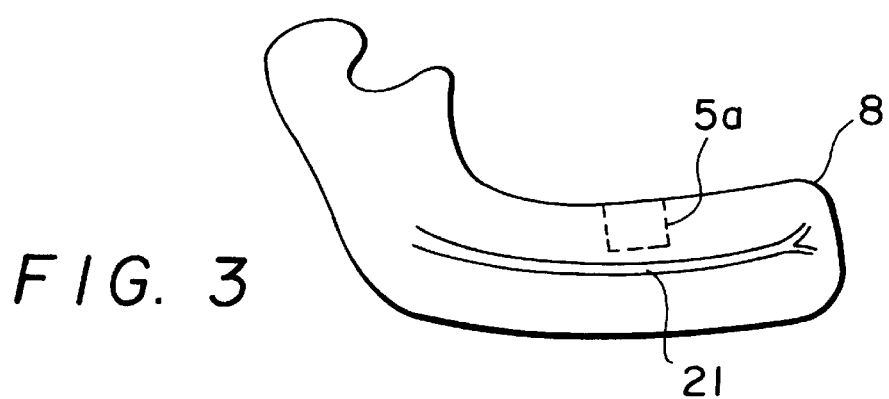
FIG. 3 is the lower jawbone of a recipient which shows an opening for the implantation of the tooth implant.

Dashed line 5A in FIG. 3 shows a hole or opening in a recipient's jawbone 8. The opening defined by dashed line 5A in FIG. 3 corresponds in size and shape to the hole or opening created in the donor's jawbone when the implant plug is removed therefrom so that the implant removed from the donor's jawbone will fit into the corresponding opening in the recipient's jawbone. As noted above, the opening in the recipient's jawbone must be large enough so that there is a space between the implant and the recipient's jawbone for a blood clot to remain therein.

Figure 4:
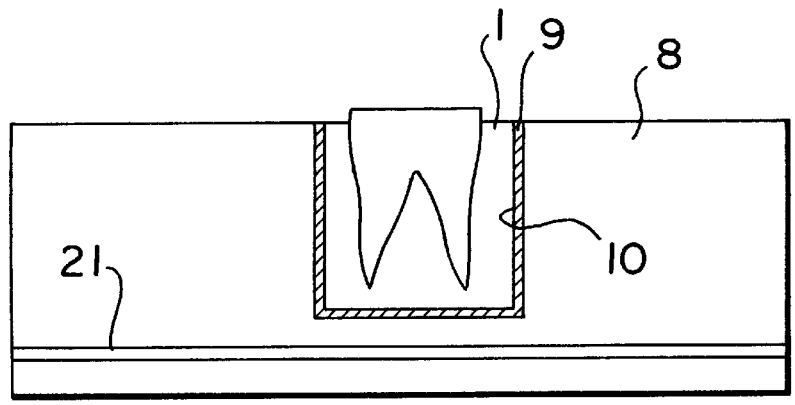
FIG. 4 shows a portion of the recipient's jawbone with the implant contained therein.

FIG. 4 shows a cross-section of an opening in the recipient's jawbone. As shown in FIG. 4, there is a small space or gap 9 between the implant 1 and the recipient's jawbone 8. Blood enters the opening during surgery and forms a clot represented by the cross-hatched zone 10. As noted previously, this clot is allowed to remain in the gap during the healing process so that the gap becomes calcified or ossified. This results in the implant being firmly and permanently anchored in the jawbone.

It will be apparent to those skilled in the art that the implant is oriented in the recipient's jawbone so that the root is in the natural anatomical position thus facilitating the attachment of a crown thereto so that the crown will be in the proper location for good dentition.

It is important that the implant should not be moved during the healing process as might occur from opposing teeth when the jaw is closed. Thus the crown of the implant should be small enough so that closing the jaw (occlusion) will not result in undesirable contact with other teeth such as opposing teeth in the jawbone. Therefore in those instances where the crown of the implant is too large, then an adjustment should be made in the implant to reduce the size of the crown. This adjustment can be made by substituting the existing crown with a new smaller crown according to known crown replacement techniques.

The above description describes implants derived from deceased persons and the use thereof in living individuals. This invention may also be practiced when an individual is both the donor and the recipient by the same methodology described above with the exceptions as noted below. This aspect of the invention is illustrated in FIGS. 5 and 6.

Figure 5:
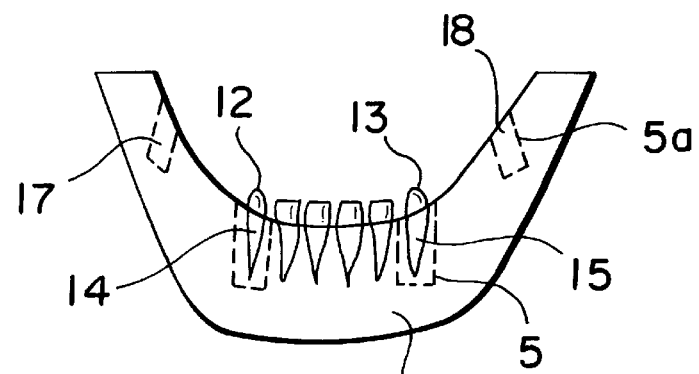
FIG. 5 shows a frontal view of the mandible which serves as the source for the implant and the opening for the implantation thereof.
Figure 6:
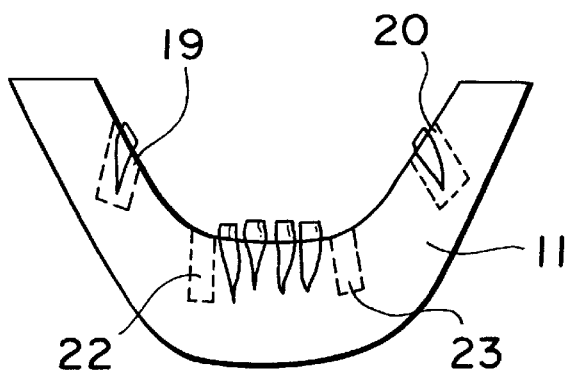
FIG. 6 shows a frontal view of the mandible of an individual from which a tooth implant has been extracted therefrom and moved to another location therein.

FIG. 5 shows the jawbone 11 of a living person which contains teeth 12 and 13 having root portions 14 and 15, respectively. Since the crown of the tooth is not necessary to practice this invention, it may be separated from the root so that the implant lacks a natural crown. The implant may be removed and the opening prepared for implantation as previously described above with respect to FIGS. 1–4. However, when the donor and recipient are the same living individual, the implant is harvested and immediately implanted into the opening. Implantation takes place as discussed above with respect to FIG. 4 so that a clot remains in the gap between the implant and the jawbone. Thus, this aspect of the invention is exemplified by removing two implants, each of which contains root 14 and 15, respectively, along with the surrounding bone tissue by the methodology previously described so that the implants fit into corresponding openings 17 and 18. The implants indicated by reference numerals 19 and 20 are shown in place in FIG. 6. Openings for holes 22 and 23 remain after the implants have been implanted as shown in FIG. 6. A blood clot is left within these holes so that they will eventually be replaced by regenerated bone tissue so as to fill the hole.

The implant is not treated for storage when the donor is also the recipient since implantation takes place immediately after harvesting. Thus, in this case, the periodontal membrane and ligament will normally remain alive whereas when the implant is taken from a deceased individual for storage and later use, the periodontal ligament is removed in the process of sterilization which includes decalcification, freezing and drying (DFTB) or lyophilization.

When the periodontal membrane is left in tact, it is surrounded by the bone. If the periodontal membrane is lost such as when it is reabsorbed by the body, calcification will occur to produce a tooth-bone calcified bond between cementum and alveolar bone.

It will be appreciated by those skilled in the art that due consideration must be given to specific anatomical details of the jaw, including nerves associated therewith, when practicing this invention. Thus, the surgical procedure must not damage the nerve contained within the inferior canal 21 shown in the recipient's jawbone 8 in FIG. 3. Consequently, the size and shape of the implant to be inserted into the recipient should be evaluated so that a correspondingly shaped opening can be prepared in the recipient's jawbone which does not interfere with the nerves associated with the jawbone. For example, if the patient has a mandibular alveolar process measuring 13 mm from the top to bottom, the length of the implant and corresponding opening for receiving the implant should be no longer than about 8 mm in order to avoid interference with the inferior alveolar nerve. In the case of a superior alveolar process (e.g., when implanting into the maxilla or upper jawbone) there should be pre-measurement of the remaining bone below the maxillary sinuses or the maxillary tuberosity dimensions which are the most likely areas to receive the implant.

Since this invention involves implantation of bone tissue in a living organism, the usual precautions and guidelines apply as would apply to the transplantation of bone blades and the like. However, this process is more simple since the implant would be immobilized under the gingivae (e.g., by stitching or similar method for joining tissue after surgery). Thus, this method eliminates the need for steel wires or other means for immobilizing the bone prior to calcification.

A crown may be attached to the implant upon completion of the implantation surgery, preferably after a period of healing (usually about 6 months after implantation surgery).

While the present invention been described in terms of certain preferred embodiments, one skilled in the art will readily appreciated that various modifications, changes, omissions and substitutions may be made without departing from the spirit thereof. It is intended, therefore, that the present invention be limited solely by the scope of the following claims.

What is claimed is:

1. A method for replacing a missing tooth with a tooth implant in a person's jawbone which comprises:

procuring a natural tooth implant obtained from the jawbone of a donor person; said implant being a unit which comprises the root of a donor's tooth without the crown attached thereto and an attached portion of donor jawbone surrounding said root;

surgically forming a receiving hole in the jawbone of a recipient person who is to receive said implant, said receiving hole being large enough to receive said implant therein with a gap between said implant and the jawbone of said recipient person;

implanting said tooth implant into said receiving hole, said implant being oriented in said hole so that a crown can afterwards be affixed to the root of said implant; and forming a blood clot within said gap and maintaining said clot within said gap until said gap becomes ossified with bone thereby joining said implant to said recipient person's jawbone.

2. The method of claim 1 wherein said donor jawbone surrounding said root defines a geometric shape and said receiving hole has the same shape as the implant with the receiving hole being larger than said implant to create said gap for the blood clot.

3. The method of claim 2 wherein the donor jawbone circumferentially surrounds said root whereby said implant is in the form of a cylindrical plug.

4. The method of claim 1 wherein said donor is a deceased person and connective tissue is removed from said implant and said implant is washed, sterilized, lyophilized and then stored in a sterile condition before procurement for implantation.

5. The method of claim 4 wherein a plurality of implants are obtained and stored in a tooth bank and the implant is procured by selecting one of the implants from said tooth bank.

6. The method of claim 4 wherein the receiving hole is prepared and allowed to heal before implantation of the tooth implant.

7. The method of claim 1 wherein the donor is the same individual as said recipient and said implant is obtained from a tooth at one location in the donor's jawbone and is implanted into another location of said donor's jawbone.

8. The method of claim 7 wherein root canal surgery is performed on said root before implantation into said recipient.

9. The method of claim 7 wherein the receiving hole is prepared and allowed to heal before implantation of the tooth implant.

10. The method of claim 7 wherein the implant is obtained and inserted into the receiving hole in a single surgical procedure without storage of said implant.

11. The method of claim 1 wherein root canal surgery is performed on said root before implantation into said recipient.

12. A method for making a sterile lyophilized tooth implant which includes the root of a natural tooth with the crown portion of said tooth removed therefrom and an attached portion of jawbone surrounding said root;

said method comprising separating the crown from said root and removing said root from the jawbone of a person along with an attached surrounding portion of said jawbone to form said implant; and removing connective tissue from said implant and washing, sterilizing and lyophilizing said implant.

13. The method of claim 12 which further comprises storing said tooth in a sterile condition for future implantation.

* * * * *